US008911424B2

(12) United States Patent
Weadock et al.

(10) Patent No.: US 8,911,424 B2
(45) Date of Patent: Dec. 16, 2014

(54) METHODS AND DEVICES FOR PREVENTING CATHETER RELATED URINARY TRACT INFECTIONS

(75) Inventors: Kevin Weadock, Hillsborough, NJ (US); Amit Khanolkar, Jacksonville, FL (US)

(73) Assignee: Ethicon, Inc., Somerville, NJ (US)

( * ) Notice: Subject to any disclaimer, the term of this patent is extended or adjusted under 35 U.S.C. 154(b) by 136 days.

(21) Appl. No.: 13/023,724

(22) Filed: Feb. 9, 2011

(65) Prior Publication Data

US 2012/0203211 A1 Aug. 9, 2012

(51) Int. Cl.
*A61M 27/00* (2006.01)
*A61M 25/00* (2006.01)
*A61L 29/14* (2006.01)
*A61L 29/16* (2006.01)

(52) U.S. Cl.
CPC .......... *A61M 25/0017* (2013.01); *A61L 29/145* (2013.01); *A61L 29/16* (2013.01); *A61M 2025/0019* (2013.01); *A61M 2025/0056* (2013.01); *A61L 2300/404* (2013.01)
USPC ............................ 604/544; 604/263; 604/268

(58) Field of Classification Search
USPC ......... 604/178, 263, 265, 517, 523–539, 544, 604/268
See application file for complete search history.

(56) References Cited

U.S. PATENT DOCUMENTS

| | | | | |
|---|---|---|---|---|
| 1,383,058 A * | 6/1921 | Atkin | .............................. | 24/281 |
| 1,853,473 A * | 4/1932 | Terwilliger et al. | ............ | 285/253 |
| 4,175,564 A * | 11/1979 | Kwak | ........................... | 604/171 |
| 4,295,689 A * | 10/1981 | Licht | ............................ | 384/103 |
| 4,623,329 A * | 11/1986 | Drobish et al. | ................. | 604/29 |
| 4,784,647 A | 11/1988 | Gross | | |
| 4,915,694 A * | 4/1990 | Yamamoto et al. | ........... | 604/180 |
| 5,049,140 A * | 9/1991 | Brenner et al. | ............... | 604/266 |
| 5,266,073 A * | 11/1993 | Wall | .............................. | 623/1.2 |
| 5,352,236 A * | 10/1994 | Jung et al. | ..................... | 606/194 |
| 5,505,695 A * | 4/1996 | Eplett, Jr. | ..................... | 604/544 |
| 5,620,424 A * | 4/1997 | Abramson | .................... | 604/265 |
| 5,746,723 A * | 5/1998 | Freeman et al. | .............. | 604/178 |
| 5,833,665 A | 11/1998 | Bootman et al. | | |
| 5,906,600 A * | 5/1999 | Bahr | ............................ | 604/265 |
| 6,676,095 B2 * | 1/2004 | Dal Pra' | ..................... | 248/230.3 |
| 6,685,697 B1 * | 2/2004 | Arenberg et al. | .......... | 604/890.1 |
| 6,765,122 B1 * | 7/2004 | Stout | ............................... | 602/41 |
| 7,947,021 B2 * | 5/2011 | Bourne et al. | ................ | 604/265 |

(Continued)

FOREIGN PATENT DOCUMENTS

WO WO 2009004626 A2 * 1/2009

*Primary Examiner* — Loan H Thanh
*Assistant Examiner* — Joshua Lee
(74) *Attorney, Agent, or Firm* — E. Richard Skula

(57) ABSTRACT

Methods and devices for preventing urinary tract infections in catheterized patients are disclosed. The device may be a cylindrically shaped antimicrobial hydrogel having a central opening and a slit along its length so that it can be applied directly over a previously inserted urinary catheter. An optional locking mechanism disposed about the slit can be used to secure the antimicrobial device to a catheter shaft. The antimicrobial device has features that conform to tissues near both male and female urethral openings. The inner surface of the device is adapted to provide for releasable engagement with the shaft of the urinary catheter. In one embodiment, the device may be placed on a urinary catheter prior to inserting the catheter in a patient. Locking fittings to secure the antimicrobial device against the urethral opening may also be used. Antimicrobial agents can be incorporated within the hydrogel or coated onto its surface.

15 Claims, 14 Drawing Sheets

(56) References Cited

U.S. PATENT DOCUMENTS

| | | |
|---|---|---|
| 2004/0106912 A1 | 6/2004 | Rosinskaya et al. |
| 2004/0225264 A1* | 11/2004 | Bourne et al. ............... 604/265 |
| 2009/0005750 A1* | 1/2009 | West ...................... 604/385.03 |
| 2009/0104254 A1* | 4/2009 | Sinko et al. ................. 424/450 |
| 2010/0298754 A1* | 11/2010 | Ostfeld et al. ............... 604/6.16 |
| 2011/0264057 A1* | 10/2011 | Eversull et al. .............. 604/265 |

* cited by examiner

CONTROL film lacking MSS antimicrobial agent

TEST film containing MSS antimicrobial agent

METHODS AND DEVICES FOR PREVENTING CATHETER RELATED URINARY TRACT INFECTIONS

FIELD OF THE INVENTION

The present invention is generally related to a system and method for reducing the incidence of urinary tract infections in humans, and more specifically to devices that can be used with urinary catheters to reduce the incidence of urinary tract infections.

BACKGROUND OF THE INVENTION

Infections contracted or acquired in hospitals and other health care facilities are the fourth largest killer of people in the United States. Each year in this country, almost two million patients contract infections in hospitals, and an estimated 103,000 of those patients die as a result. This number is as large as the combined totals of deaths from AIDS, breast cancer, and auto accidents. These deaths are largely due to respiratory system infections, urinary tract infections, catheter related infections, and surgical site infections resulting from accidental exposure to pathogens, breach of the duty or standard of care including carelessness or inattention by healthcare providers, failure to adhere to protocols, and/or deficient infection control procedures. The risk of urinary tract infection is known to be increased when catheterization of the urethra is required to remove urine from the bladder.

Conventional indwelling urinary catheters, which are used in approximately 20 percent of short-term care patients during their hospitalization or institutionalization, confer and present a predisposition to urinary tract infections. Catheter associated urinary tract infection (UTI) is the most common type of hospital-acquired infection, accounting for approximately 40 percent of such infections, and for most of the 900,000 patients with nosocomial bacteruria in United States hospitals and health care facilities each year. Adverse consequences associated with UTIs are significant and include local and systemic morbidity, secondary bloodstream infection, death, a reservoir of drug-resistant microorganisms, and increased health care costs.

It is generally accepted in this field that if a urinary catheter remains in place long enough, an infection is inevitable because, inter alia, biofilm formation typically occurs along the external and internal catheter surfaces. Host defenses have a difficult time preventing biofilm formation and the ascension of organisms into the bladder along the biofilm. The prevailing standard of care for the general treatment of urinary tract infections is the use of antibacterial drugs, including antibiotics. The length of treatment and choice of drug depend on the patient's medical history and the results of "mid-stream" urine tests that help identify the offending bacteria. The drugs most often and conventionally used to treat routine, uncomplicated urinary tract infections include trimethoprim sulfamethoxazole, nitrofurantoin, ampicillin, amoxicillin, ciprofloxacin, ofloxacin, norfloxacin, and trovafloxin.

In order to reduce the number of urinary tract infections caused by urinary catheterization, catheter manufacturers have developed antimicrobial coated or impregnated versions of the catheters. One known antibacterial catheter features a site-specific controlled release of nitrofurazone, which significantly reduces UTIs associated with catheter use. Nitrofurazone has been found to be effective against common gram-positive and gram-negative bacteria. This specialized coating is known to inhibit bacterial adherence and sustain the integrity of the urethral mucosa. Surprisingly, research has shown no clinically significant nitrofurazone resistance after over 50 years of use. Another conventional anti-microbial catheter uses a silver alloy coating and hydrogel. The occurrence of urinary tract infections has been found to be 3.7 times greater in patients catheterized with a standard catheter than in patients receiving catheters having the silver alloy coating and hydrogel. However, one disadvantage of antimicrobial catheters is that they can cost significantly more than the typical, conventional latex urinary catheter. As a result, clinicians and hospitals are reluctant to use them unless a sudden rise in the number of infections has occurred in the hospital or clinic, or if a drug resistant bacteria has been cultured from the patient or hospital or clinic.

There is a need in this art for a relatively inexpensive, simple to use device that can be used to inhibit bacterial growth and reduce biofilm formation on a urinary catheter near the opening to the urethra, be cost effective for all patients receiving a urinary catheter, be comfortable for the patient, and be gender specific. Such a device would provide the benefits of reducing the overall cost to the hospital or other healthcare provider and reducing the infection rate associated with UTIs, as well as providing a significant patient benefit.

SUMMARY OF THE INVENTION

Accordingly, an antimicrobial device for preventing urinary tract infections is disclosed. The device has inner and outer surfaces and first and second ends. A lumen extends from the first end to the second end so that a urinary catheter can be placed through the lumen, i.e., the device may be mounted on the catheter. The device may also have a slit that extends from the inner surface to the outer surface so as to enable placement of the device onto the shaft of a previously implanted urinary catheter. Locking mechanisms may be physically associated with the slit so as to enable secure attachment of the antimicrobial device to the catheter shaft. The device preferably has a convex or concave surface on at least one of the first or second ends so as to allow for anatomically correct approximation to male or female patients. The device is preferably made from materials that match the compliance of the tissue near the opening to the urethra. The inner surface of the device is preferably adapted to provide for releasable engagement with the shaft of the urinary catheter. The device may have first and second configurations. The device has an antimicrobial agent, and is optionally constructed from a hydrogel. The antimicrobial agent may be coated onto the surface of the device or incorporated into the device so as to preferably allow for prolonged release of the antimicrobial agent.

Another aspect of the present invention is to provide a method for preventing urinary tract infections using the above-described antimicrobial device of the present invention. The method includes identifying the gender of a patient to receive a urinary catheter, applying an antimicrobial device having ends adapted for male or female patient onto a shaft of a urinary catheter such that the end of the antimicrobial device matches the patient's gender (i.e., anatomy), inserting the catheter into the patients urethra, and then advancing the anti-microbial device until it reaches tissue proximate the urethral opening, and then securing the anti-microbial device at that point on the catheter shaft.

Yet another aspect of the present invention is an alternate method for preventing urinary tract infections. The method includes the steps of identifying the gender of a patient to receive a urinary catheter, inserting the catheter into the patients urethra, attaching an antimicrobial device of the present invention in its first configuration to the catheter shaft, manipulating the antimicrobial device to a second configuration, advancing the anti-microbial device until it reaches tissue proximate the urethral opening, and then optionally utilizing a locking mechanism to secure the anti-microbial device on the catheter shaft.

Still yet another aspect of the present invention is a device that prevents urinary tract infections by delivering an antimicrobial agent to the surface of the catheter and tissue near the opening to the urethra for sustained periods.

These and other aspects and advantages of the present invention will become more apparent from the following description and examples, and accompanying drawings.

DETAILED DESCRIPTION OF THE INVENTION

Figure 1A:
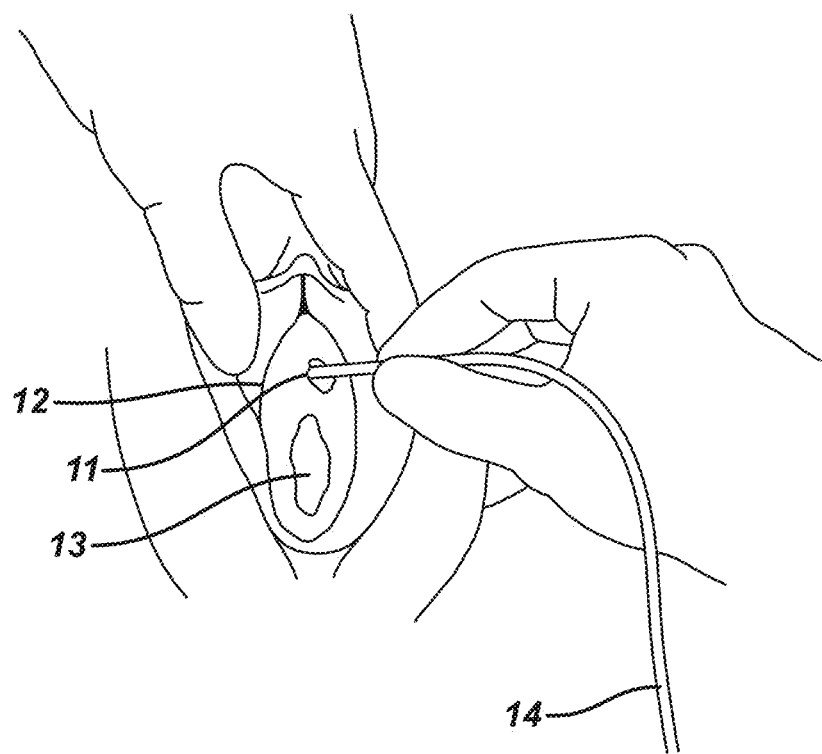
FIG. 1A is a diagrammatic illustration of a catheterization of a female urethra, along with an illustration of the adjacent female anatomy.
Figure 1B:
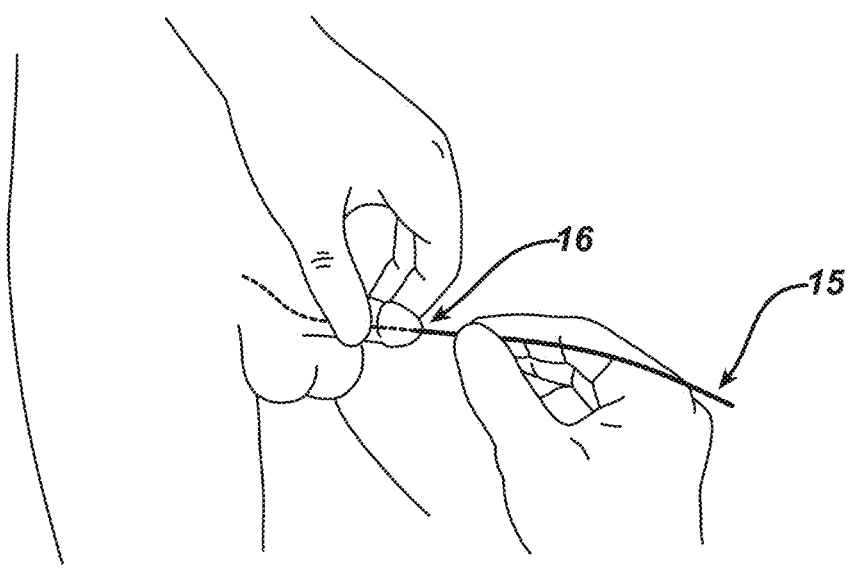
FIG. 1B is a diagrammatic illustration of the male anatomy proximate the urethral opening and the insertion of a urinary catheter into the urethral opening.

The anatomical structures surrounding the opening to the urethra in a female patient are different than the anatomical structures near the urethral opening in male patients. The differences are illustrated in FIG. 1A and FIG. 1B. As illustrated in FIG. 1A, the urethral opening 11 in the female patient is covered by labial tissue 12, and the urethral opening is in close proximity to the vagina 13 and surrounding tissues. As a result, it can be seen and it is generally recognized that a catheter 14 placed in a female urethra 11 may be more prone to infection than a catheter 15 placed in a male patient's urethra 16, since the tissue near the vagina 13 and opening to the urethra 11 is known to provide an environment conducive to the growth of bacteria. FIG. 1B illustrates a urinary catheter 15 being placed into a male urethral opening 16. It is also believed that the shorter length of a urethra in a female patient may also contribute to the higher rates of infection.

Figure 2A:
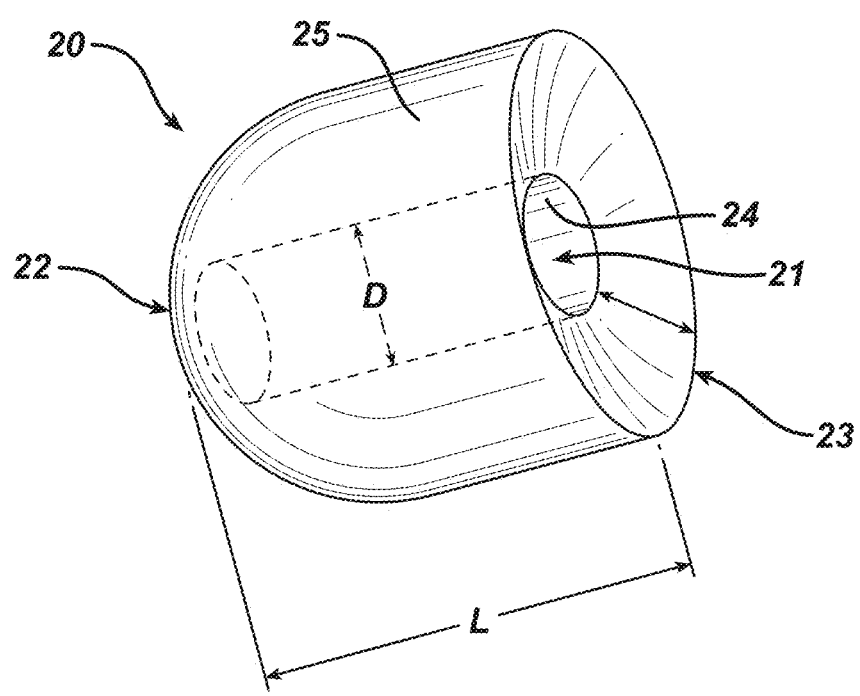
FIG. 2A is a perspective view of an embodiment of an antimicrobial device of the present invention for preventing urinary tract infections.

One embodiment of an antimicrobial device 20 of the present invention for preventing urinary tract infections is seen in FIG. 2A. The device 20 has a lumen 21 that communicates with a first end 22 and a second end 23. The lumen 21 may be centrally located about the longitudinal axis of the device, or may be offset if desired. The device has an inner surface 24 about the lumen 21 and an outer surface 25. The diameter D of the lumen 21 varies according to the outer diameter of the urinary catheter. In one embodiment, the diameter D of the lumen 21 may be slightly smaller at the first end 22 than it is at the second end 23, resulting in a tapered lumen in order to afford tighter engagement of the device onto the outer surface of a urinary catheter. The device 20 preferably has a wall thickness WT between about 0.10 inch and about 1 inch. The length of the device 20 is preferably between 0.5 and 1.0 inch. It will be appreciated that the wall thickness and length will vary depending upon a variety of factors including the diameter of the urinary catheter and gender of the patient. The wall thickness will be sufficiently thick to effectively secure the antimicrobial device to the catheter and prevent it from tearing or cracking, while the length will be sufficient to effectively cover a portion of the catheter that is exposed to contaminated tissues. The distal end of a urinary catheter can be inserted into the lumen 21 of the device 20 prior to inserting the catheter into the urethra, i.e., the device 20 may be mounted to the catheter prior to insertion of the catheter into the urethra. The narrower width or profile of the first end 22 can be gently inserted into the female vulva so as to bring the device 20 on or near tissue proximate the urethral opening. In one embodiment, the first end 22 is convexly curved with a somewhat bullet-tip shape. This end is easily inserted into the vulva of a female patient so as to provide comfortable and appropriate contact with the urethral opening. In one embodiment, the second end 23 is concavely shaped to accommodate the distal region of the male penis. This promotes proper and secure engagement of the device to the urethral opening of a male patient. In one embodiment, the device 20 has both first end 22 and second end 23 that can engage a male or female patients' urethral opening, respectively. The clinician in practice orients the device according to the patient's gender. The device 20 as illustrated in FIG. 2A is seen to have a substantially cylindrically shaped body with a rounded or bullet shaped end 22, however, the body of device 20 may have other geometric configurations including toroidal, spherical, conical, ellipsoidal and the like.

Figure 2B:
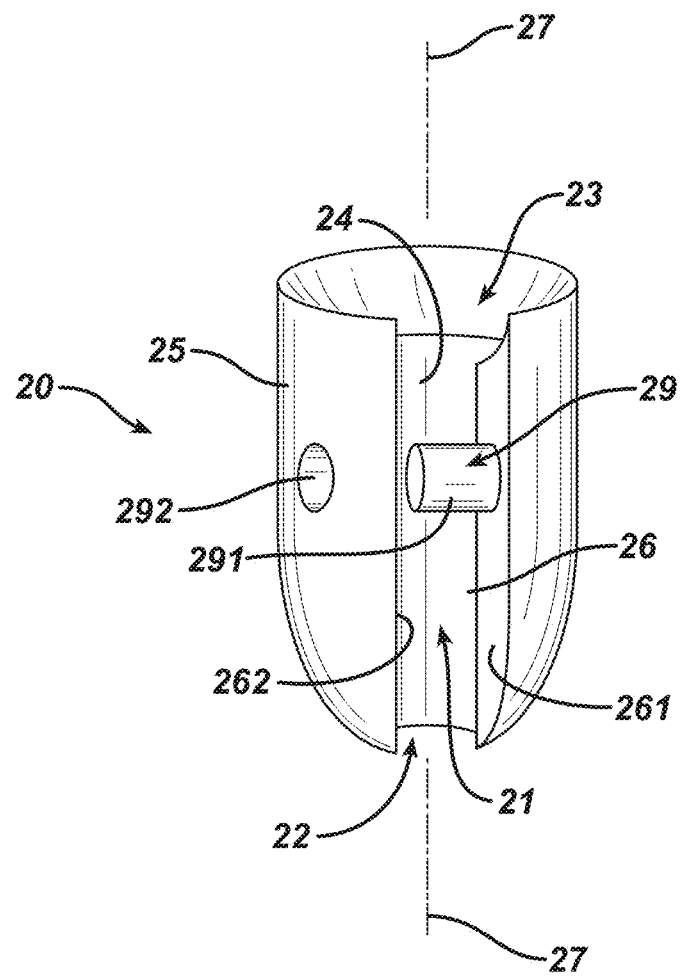
FIG. 2B is a perspective view illustrating another embodiment of the antimicrobial device of the present invention in an open position and having a locking mechanism associated with the slit to enable securement on a previously inserted urinary catheter.
Figure 2C:
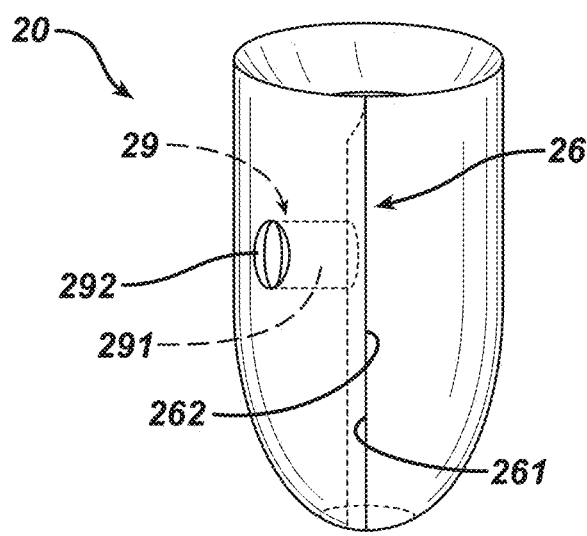
FIG. 2C illustrates the antimicrobial device of FIG. 2B in a closed position and having the locking mechanism engaged to enable securement on a previously inserted urinary catheter.

In one embodiment illustrated in FIG. 2B, the device 20 has a slit 26 that extends from the inner surface 24 to the outer surface 25 to enable "over the catheter" attachment, i.e., attaching or mounting the device 20 to the catheter shaft after the catheter has already been inserted into the urethra. The slit 26 is seen to be substantially parallel with the longitudinal axis 27 of the device 20 (i.e., radial), but may be optionally angulated (i.e., tangential or offset), and has a first surface 261 and second opposed surface 262. FIG. 2B and FIG. 2C illustrate first and second configurations (open and closed) of the device, respectively. In this embodiment, there exists an associated optional locking mechanism 29, for example within the slit 26. The device 20 can be placed over or mounted to the shaft of a catheter that has already been inserted into the bladder of a patient by opening the device 20 to a first configuration shown in FIG. 2B that illustrates a protrusion—hole coupling as a locking mechanism, and provides lateral access to the lumen 21. A protrusion 291 on the first surface 261 of the slit 26 fits into a hole 292 in the second surface 262 of the slit 26, preferably in a friction or mechanical fit manner. The hole 292 may extend completely through to the exterior surface or may be a blind hole. The device 20 is placed over (i.e., mounted to) the shaft of the catheter and the locking mechanism 29 is deployed or engaged as shown in FIG. 2C by engaging the protrusion 291 on the first surface 261 of the slit 26 in the hole 292 on the second surface 262 of the slit 26. In one embodiment, the protrusion is barbed to allow for greater holding strength. In one embodiment, the protrusion is rectangular in shape and fits into a mating slit on the other face of the slit. In another embodiment, the locking mechanism is an adhesive disposed on the first surface or second surface of the slit. In another embodiment, the locking mechanism is a strap or clamp that is wrapped around at least a portion of the periphery of the device. It will be appreciated by those skilled in the art that additional equivalent locking configurations may be used.

Figure 2D:
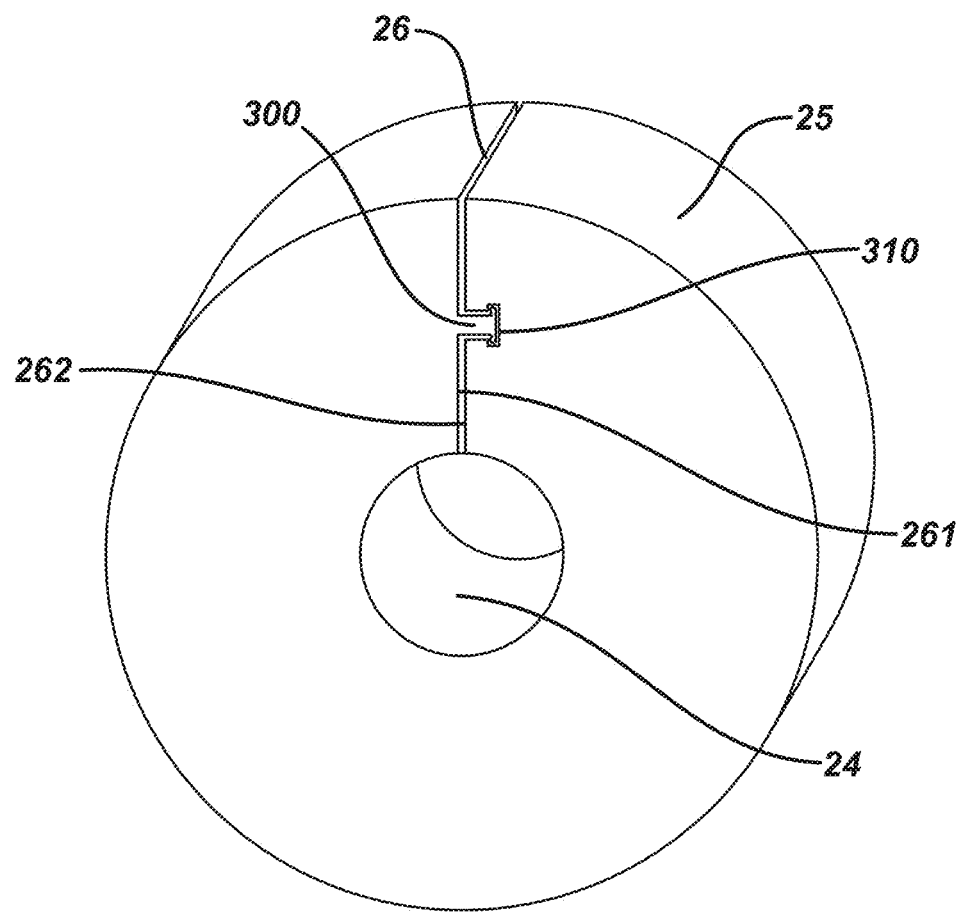
FIG. 2D illustrates a perspective view of one embodiment of an antimicrobial device having a locking mechanism, wherein the locking mechanism is in a closed position.
Figure 2E:
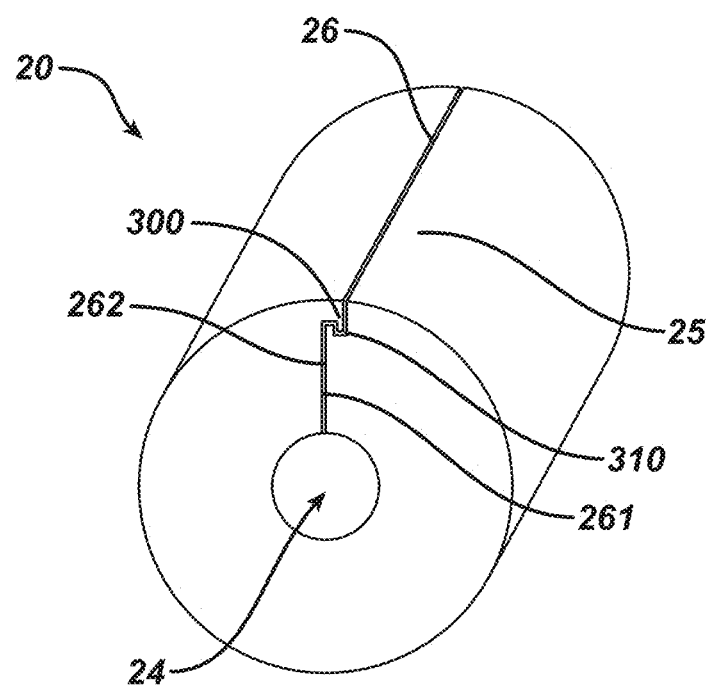
FIG. 2E illustrates a perspective view of another embodiment of an antimicrobial device having a locking mechanism, wherein the locking mechanism is in a closed position.

Referring now to FIGS. 2D-E, alternate embodiments of the device of the present invention are shown, with device 20 having a lockable mechanism comprising a ridge member 300 and corresponding mating groove 310 for engaging the ridge 300, with ridge member 300 and groove 310 disposed on opposing sides of slit 26, specifically on the first surface 261 and on the second surface 262. In one embodiment illustrated in FIG. 2D, the ridge member 300 and corresponding mating groove 310 are disposed between the inner surface 24 and outer surface 25. In another embodiment, the ridge member 300 and corresponding mating groove 310 are disposed on the edge of slit 26 in close proximity to the outer surface 25, as shown in FIG. 2E.

Figure 3A:
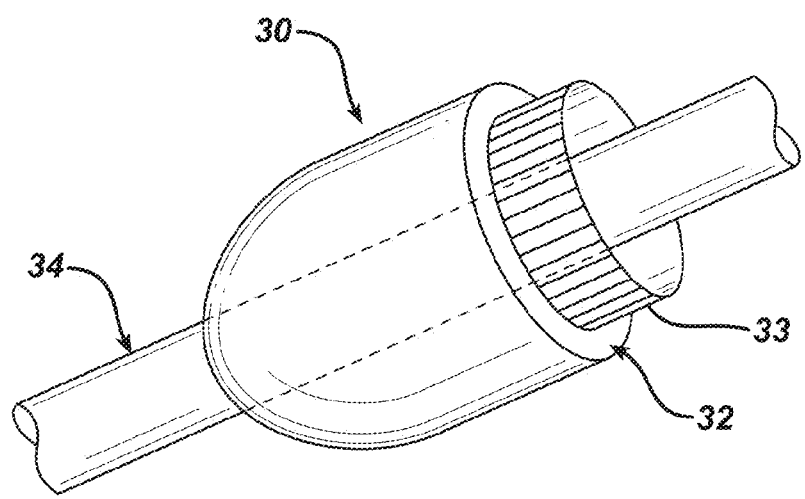
FIG. 3A is a perspective view illustrating the use of a compression fitting with an antimicrobial device of the present invention mounted on a urinary catheter.
Figure 3B:
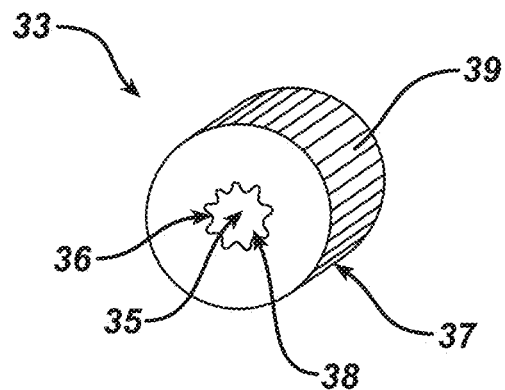
FIG. 3B is an enlarged perspective view of the compression fitting of FIG. 3A.

In one embodiment of a device 30 of the present invention illustrated in FIG. 3A, a second end 32 of the device 30 may be coupled with or used with an optional, separate compression fitting 33 so that it can be handled aseptically, as well as allowing the patient or clinician to adjust the proximity of the device 30 close to tissue proximate the opening of the urethra. In this embodiment, the device 30 and compression fitting 33 can be slid over the catheter shaft 34 prior to placement of the urinary catheter in the bladder or the device can have a slit that enables it to be placed onto a previously placed urinary catheter. For example, the device 30 may be positioned and adjusted with more or less compression against the urethral opening, depending on what the patient is comfortable with. FIG. 3B illustrates an enlarged view of fitting 33, which is placed behind the device 30 of FIG. 3A and which engages the catheter shaft through frictional contact. Fitting 33 is shown as a substantially cylindrical member having an inner lumen 35 and an outer surface 37. Frictional contact with the catheter is provided by ridges 36 or other features extending radially inwardly from or on the inner surface 38 of the fitting 33 about the lumen 35. Although not preferred, inner surface 38 may be smooth without projections of ridges. External ridges 39 can also be added to outer surface 37 to prevent the health care provider's fingers from slipping on the fitting. It will be appreciated that the fitting 33 may have other geometric configurations, including toroidal, spherical, conical, ellipsoidal and the like.

The embodiments illustrated in FIG. 3A and FIG. 3B can also be modified with a slit, such as those previously described, to enable them to be placed over or mounted to a previously placed catheter, i.e., already implanted within a patient's bladder. This is accomplished by opening the slit of the device 30 by separating the opposed surfaces so that a space or opening forms between the opposed surfaces to form a first configuration that can be placed over a catheter shaft such that the shaft is contained in the device lumen. Once the device is placed over the shaft, the device has a second configuration in which the slit is substantially closed with the opposed surfaces substantially in contact with each other. The fittings illustrated in FIG. 3A-B are preferably polymeric and can be flexible or rigid. Examples of suitable biocompatible polymers include but are not limited to silicone, polypropylene, polycarbonate, rubber, polyurethane, and polyethylene and other conventional biocompatible polymers. In one embodiment, a wrapper that is placed around or over at least a portion of the device can be used to allow the patient or caregiver to hold the device or advance it on the catheter shaft without directly touching the device with fingers or gloves that might be contaminated with bacteria. The wrapper may be a loose plastic liner or metal foil that can easily be removed after the device is positioned.

Figure 4:
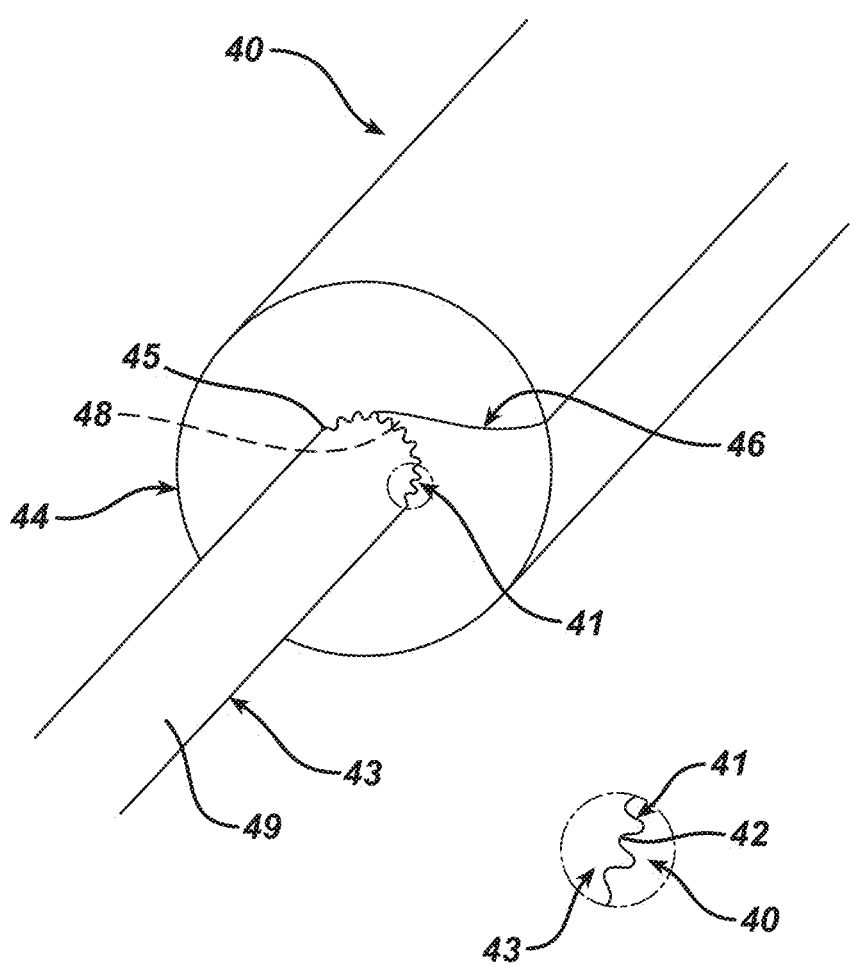
FIG. 4 is a perspective view that illustrates extensions on the inner surface of the antimicrobial device of FIG. 3A.

In one embodiment illustrated in FIG. 4, the device 40 has undulating protrusions or extensions 41 on its inner surface 42 that enable the inner surface 45 of the device 40 to be securely engaged with the outer surface 49 of a catheter 43. Preferably, the extensions 41 run along the entire length of the inner surface 45, but may be segmented or discontinuous if desired. This provides securement of the device against tissue proximate the opening to the urethra, i.e., the meatus. This is an important feature that prevents the device 40 from leaving the location on the catheter 43 which requires anti-microbial protection the most, i.e., the point nearest the tissue proximate the opening to the urethra. Also illustrated in FIG. 4 is a slit 46 that extends outwardly from the inner surface 45 of the device 40 to its outer surface 44 along the length of device 40. The slit extends out from the lumen 48 in a tangential manner to outer surface 44.

Figure 5A:
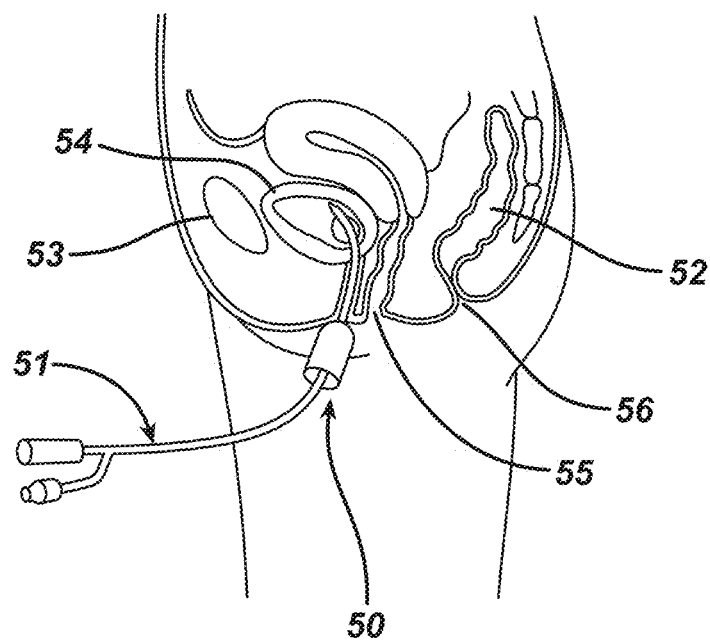
FIG. 5A is a diagrammatic illustration of the placement of a device of the present invention on a urinary catheter, wherein the catheter has been inserted into the urethra of a female patient.
Figure 5B:
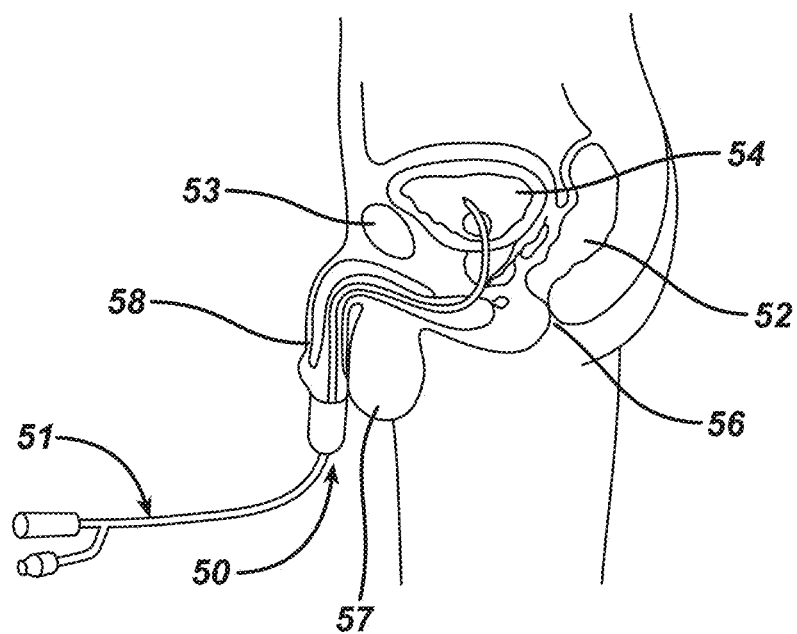
FIG. 5B is a diagrammatic illustration of the placement of a device of the present invention on a urinary catheter inserted into the urethra of a male patient.

FIG. 5A is a diagram illustrating the placement of a device 50 of the present invention over a catheter 51 that has been inserted into the tissue proximate to the opening of the urethra of a female patient. Also shown are the rectum 52, the pubic bone 53, the bladder 54, the vagina 55, and anus 56. FIG. 5B illustrates placement of the device 50 over a catheter 51 that has been placed proximate to the opening of the urethra of a male patient. Also shown are the rectum 52, the pubic bone 53, the bladder 54, the scrotum 57, the penis 58, and anus 56.

It is particularly preferred to manufacture the devices of the present invention from biocompatible hydrogels. Hydrogels are comprised of a network of natural or synthetic polymer chains that are hydrophilic, sometimes found as a colloidal gel in which water is the dispersion medium. Hydrogels are highly absorbent and can contain over 99% water. Hydrogels also possess a degree of flexibility very similar to natural tissue, due to their significant water content.

Compliance is a material property that is often used to describe the stiffness, rigidity, or elasticity of a substance. The use of these terms can be confusing, since stiffness and rigidity are the opposites of elasticity and compliance—something that is highly compliant or elastic tends to exhibit low stiffness and rigidity.

The quantitative measure of these qualities is often the Elastic Modulus, which is a measure of the increase in stress when strain is applied to a material, or $$E = \sigma/\epsilon,$$

Where E=Modulus, σ=stress, and ϵ=strain. There are several ways to measure the elastic modulus used by those skilled in the art of hydrogel synthesis and testing, including tensile testing, rheological measurements, and atomic force microscopy (AFM). The compliance of a material is the reciprocal of the modulus, i.e., $1/E$ or $\epsilon/\sigma$.

The compliance of the hydrogel is preferably matched to the compliance of the tissue that it is applied to, i.e., the tissue near the opening of the urethra. Values for such compliances are widely known and available in the art. The compliance matching to the urethral opening tissue prevents or minimizes any discomfort the device might cause to the patient. In one embodiment, the antimicrobial device is a hydrogel comprised of a silicone material and having one or more antimicrobial agents dispersed within the hydrogel. In other embodiments, the hydrogel can be comprised of carboxymethylcellulose, chitin, carboxymethyl starch, carboxymethyl cellulose, hydroxyalkylmethyl cellulose, hydroxypropyl cellulose; nonionic types of hydrogels such as polyvinyl alcohol and polyvinyl ethers; cationic types of hydrogels such as polyvinyl pyridine, polyvinylpyrrolidone, polyvinyl morpholinione, and N,N-dimethylaminoethyl or N,N-diethylaminopropyl acrylates and methacrylates, or respective quaternary salts thereof. In addition to hydrogels, other biocompatible polymers may also be used to make the devices of the present invention. These polymers include polyethylene oxide (PEO), gelatin; polyacrylamide, including polydimethylacrylamide (PDMA), polyacrylic acid, polyethers such as polyethylene glycol, and polypropylene glycol, and the like and equivalents thereof.

The devices of the present invention will contain or provide sufficient amounts of antimicrobial agents to effectively prevent or reduce the chance of infection. The antimicrobial agents added to the hydrogels or other polymers used to make the devices of the present invention include conventional antimicrobials such as chlorhexidine gluconate, iodine, chlorhexidine acetate, silver, silver salts, silver halides such as silver iodide and silver chloride, octinidene, triclosan, benzalkonium chloride, alcohols, and antibiotics. Antimicrobial concentrations of 1-10,000 ppm in the polymer are typically suitable for preventing infection. However, other antimicrobial agents known to those skilled in the art of microbiology may also be used.

In one embodiment, addition of the antimicrobial agent to the composition can be performed prior to placing the composition in a mold to make the device. The antimicrobial agent can be added by mixing or blending it within the hydrogel prior to adding the composition to a mold that will make the desired device. The antimicrobial agent can also be added to the device after the molding process by immersing the device in a solution containing the antimicrobial agent. The antimicrobial agent can diffuse into the hydrogel until the desired dose is achieved. The desired dose of antimicrobial agent can be obtained by varying the time the device is immersed in the solution or by varying the concentration of the antimicrobial agent in the solution.

In another embodiment, the device containing an antimicrobial agent is subjected to a coating process. This coating process would add a coating containing an antimicrobial agent alone or a mixture of the antimicrobial agent and a substance such as PVP to provide rapid release of the antimicrobial agent. The coating process can be performed by immersing the device in a solution or dispersion of the antimicrobial agent. Alternatively, the coating containing the antimicrobial agent can be sprayed onto the surface of the device. This embodiment would allow for a rapid release of the antimicrobial agent as well as sustained release. In another embodiment, the device would be sprayed with a thin layer of polymer that did not have an antimicrobial agent in it. This layer would be used to control the rate of diffusion of the antimicrobial agent out of the device. Suitable polymers for this coating would be PVP and silicone. Although not particularly preferred, the devices of the present invention may have antimicrobial agents contained only in the coating.

Other conventional therapeutic agents may be added to the hydrogels and polymers used to manufacture the devices of the present invention (including the coatings). These therapeutic agents include anti-inflammatory agents such as steroids and non-steroidal anti-inflammatory agents, antifungal agents, analgesics, or ointments to reduce pain. The therapeutic agents are present in therapeutically effective amounts. In another embodiment, a fragrance is added to the hydrogel composition so as to mask any smell of urine or related degradation products such as ammonia.

In one embodiment, the device is comprised of a suspension of silver halide in polyvinylpyrrolidone (PVP). Silver has long been known to be a useful antimicrobial agent in or on catheters, dressings and sutures. It has an anti-microbial effect against fungi, gram negative bacteria, and gram positive bacteria. Its efficacy allows it to provide a therapeutic effect with little to no toxicity. It also has a low potential for developing resistant organisms. It is compatible with standard known antibiotics and its low aqueous solubility allows for sustained release. The aqueous solubilities of silver halides (chloride, bromide and iodide) are shown in Table 1.

TABLE 1

| Compound | Solubility (g/100 g $H_2O$) |
|---|---|
| Silver Chloride | 0.00019 |
| Silver Bromide | 0.000014 |
| Silver Iodide | 0.000003 |

The antimicrobial activity of silver iodide stems from the widely known activity of the silver ion (Ag+). Silver ions demonstrate antimicrobial activity via a number of mechanisms resulting in a range of effects from inhibition of growth, loss of infectivity, and cell death. The mechanism depends on both the concentration of silver ions present and the sensitivity of the microbial species to silver. Contact time, temperature, pH and the presence of free water all impact the rate and extent of antimicrobial activity. Silver ions interact with a number of components of bacterial, protozoal and fungal cells. The kinetics of antimicrobial activity vary depending on the source of silver ions with silver derived from ion exchange processes demonstrating delayed activity compared with that derived from silver salts. Mechanistic studies have shown that silver ions interact with sulfhydryl (—SH) groups of proteins as well as the bases of DNA leading either to the inhibition of respiratory processes or DNA unwinding. Other reported modes of action include inhibition of cell division and damage to bacterial cell envelopes and interaction with hydrogen bonding processes. Interruption of cell wall synthesis resulting in loss of essential nutrients has been shown to occur in yeasts and in other fungi. The interaction with —SH groups has been used to explain the antiviral activity of silver ions.

In one embodiment, the formulation used to make the device is comprised of a suspension of monomeric silver iodide in polyvinylpyrrolidone and a mixture of monomers with one or more vinyl groups that can be polymerized to form an interpenetrating network of cross-linked polymer chains. Monomeric or polymeric components without a functional vinyl group can also be included in the formulation so that they are physically trapped in the polymer network. The antimicrobial agent added to the formulation is a monomeric silver suspension (MSS) and is in the form of a silver halide (iodide, bromide or chloride) complexed with a dispersing agent in the form of a polymer with functional groups with lone pair of electrons like polyvinylpyrrolidone (PVP), polyvinylalcohol (PVA), hydroxyalkylmethylcellulose polymers, polyethylene oxide (PEO), polysaccharides, such as starch, pectin, gelatin; polyacrylamide, including polydimethylacrylamide (PDMA), polyacrylic acid, organoalkoxysilanes such as 3-aminopropyltriethoxysilane (APS), methyl-triethoxysilane (MTS), phenyl-trimethoxysilane (PTS), vinyl-triethoxysilane (VTS), and 3-glycidoxypropyltrimethoxysilane (GPS), polyethers, such as polyethylene glycol, polypropylene glycol, boric acid ester of glycerin (BAGE), silicone macromers having molecular weights greater than about 10,000 and comprising groups which increase viscosity, such as hydrogen bonding groups, such as but not limited to hydroxyl groups and urethane groups and mixtures thereof. The dispersing agent complexes with the silver ion and inhibits the agglomeration and particle size growth as shown below.

dimethoxyphenyl) methanone. Other synonyms for CGI 819 are MolPort-001-769-891, CID164459, OR7002, and phosphine oxide.

In order to prevent dehydration of the hydrogel during storage, the hydrogel device is preferably packaged in a suitable package with a lid that can be easily be peeled off by the clinician, for example foil. The device can be packaged in a suitable packing solution consisting of DI water and other additives like surfactants and pH buffers. The pH, conductivity and osmolality of the packing solution will be designed for suitable shelf life stability of the device. The device can be packaged in a sealed glass vial or a plastic blister package sealed with a composite foil using a heat seal process. Sterilization is preferably accomplished by conventional autoclaving. Other conventional methods of sterilization like gamma irradiation or ultraviolet irradiation can also be used.

The following examples are illustrative of the principles and practice of the present invention, although not limited thereto.

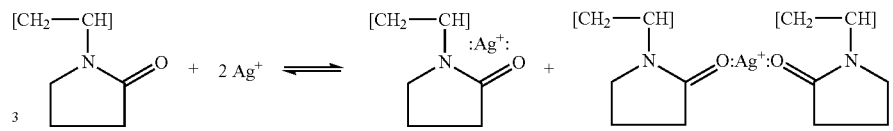

The antimicrobial agent is preferably released from the device by diffusion from the device over a sustained period of time, preferably between 1 and 14 days. In one embodiment, the device is comprised of nanoparticles of a silver halide, the halide being selected from the group consisting of a bromide, iodide, and chloride. The low aqueous solubility of silver allows for sustained release.

The formulation can be designed such that is can be polymerized using heat, light or a combination of the two. A typical formulation is composed of the following components shown in Table 2.

TABLE 2

| Component | Function | Typical Components |
|---|---|---|
| Monomer | Polymerizes during cure. | Hydroxyethylmethacrylate (HEMA), silicones, dimethylacrylamides (DMA). |
| Polymers | Trapped in the interpenetrating network (IPN). | PVP, PVA. |
| Crosslinker | Difunctional or Trifunctional groups crosslinks with polymer chains. | Ethylene glycol dimethacrylate. |
| Initiator | Initiates the polymerization reaction when subjected to heat, light or a combination of the two. | CGI 819, CGI 1850, AIBN. |
| Antimicrobial agent | Releases from the device at a desired rate to provide efficacy against microorganisms. | Silver iodide, silver bromide, silver chloride or combinations thereof. |
| Dye (Optional) | Tinting of the hydrogel. | Various |

Initiators listed in Table 2 are well known to polymer chemists. For example, CGI 819 is also known as [(2,6-dimethoxybenzoyl)-(2,4,4-trimethylpentyl)phosphoryl]-(2,6-

EXAMPLE 1

A monomeric silver suspension (MSS) was made from a dispersion of silver iodide in poly (vinyl pyrrolidone) (PVP K12) formed by spray drying of the silver iodide dispersion in PVP solution. The process of synthesizing MSS involved dissolving silver nitrate and sodium iodide in PVP K12-DI water solution. The silver nitrate-PVP K12 solution was then added to the sodium iodide-PVP K12 solution in a controlled manner, which resulted in the formation of silver iodide dispersion in the PVP K12 solution (MSS solution).

The MSS solution was then spray dried to obtain dry MSS powder. The physicochemical attributes of MSS are shown in Table 3.

TABLE 3

| Attribute | Details/Specification |
|---|---|
| CAS Numbers | PVP K12: 9003-39-8; AgI: 7783-96-2 |
| Molecular Weight | Approx. 2500 g/mol. |
| Molecular Formula | $(C_6H_9NO)_n$ AgI |
| Molecular Structure | —[$CH_2$—CH]— \\ O=⟨N⟩ + AgI |
| Appearance | White to yellowish white powder |
| Clarity of a 5% solution | Yellowish clear solution |
| PVP K12 identification | Positive identity result |
| Silver content (µg Ag/g MSS) | 6800 ± 680 |
| Iodide content (µg I/g MSS) | 9100 ± 910 |
| Silver to iodide molar ratio | ≤0.95 |
| Water content (gravimetric) | ≤5.0% |
| Silver iodide particle size ($D_{90\%}$) | ≤65 nm |

Figure 6A:
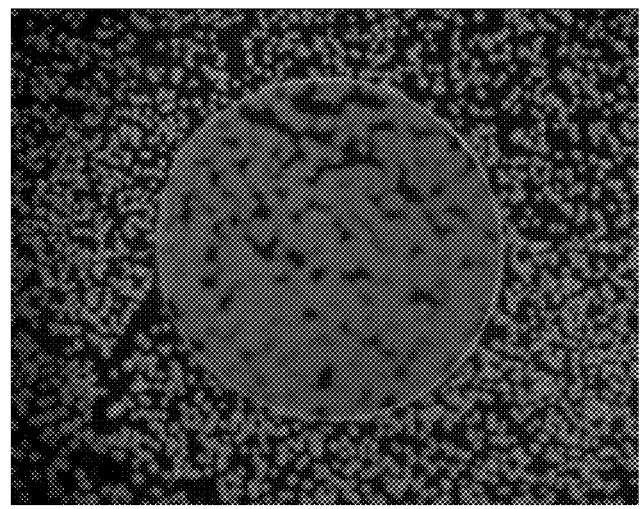
FIG. 6A is a photograph of a zone of inhibition test against *Staphylococcus Aureus* for a hydrogel film sample without an antimicrobial agent.
Figure 6B:
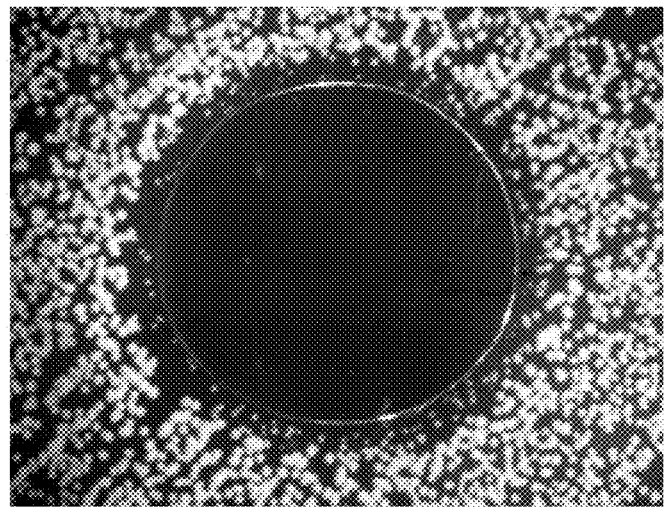
FIG. 6B is a photograph of a zone of inhibition test against *Staphylococcus Aureus* for a hydrogel film sample containing a silver iodide antimicrobial agent.

The dried MSS was then added to other monomer components of the formulation to form a reactive monomer mix (RMM) containing 0.01% Blue HEMA, 0.14% CGI 819, 0.45% EGDMA, 0.90% Norbloc, 3.6% PVP K90, 5.10% HEMA, 13.2% m-PDMS 1000, 18.0% SiMAA2, and 18.6% DMA, 29% t-amyl alcohol, 5.25% PVP K12, and 5.75% MSS. The RMM was then added to the mold and then photopolymerized using a visible light source (peak at 420 nm) at an intensity of 5 mW/cm$^2$ at 55° C. The cured polymer was then hydrated by successive treatments of DI water, 70% 2-propanol and DI water. The water content of the final hydrogel film was approximately 47% by weight. The utility of the films in creating a zone of inhibition against *Staphylococcus aureus* is illustrated in FIG. 6A and FIG. 6B. FIG. 6A is a photograph of a zone of inhibition assay for a control film sample made from a RMM that did not have the MSS. Bacteria are still visible under the film, indicating a lack of antimicrobial activity. FIG. 6B is a photograph of a zone of inhibition assay for a hydrogel film sample made from a RMM containing the MSS. The absence of notable bacterial growth underneath the film indicates antimicrobial activity.

EXAMPLE 2

Urinary catheterization is the procedure of inserting a catheter through the urethra into the bladder to remove urine. Sterile, disposable conventional catheterization sets are available in clinical settings and for home use. These sets contain most of the items needed for the procedure, such as antiseptic agents, perineal drapes, gloves, lubricant, specimen container, label, and adhesive strips. Local anesthetic gel, lubricant, catheter, and drainage system may additionally be required. To perform the procedure, the patient is placed in a horizontal recumbent position and the tissue near the urethral opening is washed with a mild soap and water and patted dry. Using aseptic technique, an anesthetic gel is applied to the tissue near the urethral opening. In one embodiment of the present invention, the antimicrobial device is then removed from its packaging by the patient or health care provider and placed over the distal tip of the catheter by pushing the catheter through the lumen of the antimicrobial device. Optionally, a polymeric compression fitting or lock washer illustrated in FIG. 3A or FIG. 3B is also utilized at this time. The catheter shaft is inserted into the lock washer or compression fitting prior to inserting the catheter into the lumen of the antimicrobial device.

The antimicrobial device and optional lock washer or compression fitting are then advanced up the catheter shaft about 15-20 cm. The distal most 8-12 cm of the catheter is then lubricated prior to gently inserting the catheter with a smooth continuous motion into the urethra until it is observed that urine begins to flow. The catheter is then advanced an additional 5 cm into the urethra before inflating the associated catheter balloon with 5-10 ml of sterile solution to hold the catheter in place. The catheter is then connected to a drainage system. The catheter is anchored to the thigh of the patient with hypoallergenic adhesive to prevent urethral traction. The antimicrobial device and optional lock washer or compression fitting are then moved along the catheter shaft until at least one of the surfaces on the antimicrobial device contact the tissue near the urethral opening.

In one embodiment, the antimicrobial device is applied over the catheter after the catheter has been inserted into the patient and anchored to the patient's thigh. In this embodiment, the antimicrobial device is removed from the package by the patient or health care provider and gently manipulated to an "open" configuration. In this open configuration, the antimicrobial device is wrapped around or mounted to the catheter shaft at a point where the catheter is close to the urethral opening. The configuration of the antimicrobial device is then changed by the patient or health care provider to be in a "closed" configuration, i.e., it is completely around the catheter shaft. If necessary, the antimicrobial device is moved on the catheter shaft so that at least one of the end surfaces on the antimicrobial device contacts tissue near the urethral opening. Optional locking means when present on the antimicrobial device are then deployed so that the antimicrobial device is secured to the catheter shaft proximate tissue near the urethral opening.

The devices of the present invention have many advantages including a simple method of applying a device to a urinary catheter shaft that can deliver antimicrobial agent to the tissue near a urethral opening during catheterization. The devices and methods will result in a reduced likelihood of infections occurring, resulting in better patient outcomes and decreased healthcare costs.

Although this invention has been shown and described with respect to detailed embodiments thereof, it will be understood by those skilled in the art that various changes in form and detail thereof may be made without departing from the spirit and scope of the claimed invention.

What is claimed is:

1. A device for preventing catheter-related urinary tract infections, the device comprising:
a cylindrical member having first and second opposed ends, wherein the first end is convex and the second end is concave, a lumen extending through the member, an inner surface about the lumen such that the lumen communicates with openings in the first and second ends, wherein the inner surface has a circumference and a length, and an outer surface, wherein the inner surface and the outer surface define a body wall; a slit defining a plane that extends from the inner surface to the outer surface of the member through the body wall for at least a portion of the length of the device, the slit having opposed facing sides having opposed surfaces, wherein the slit extends out from the lumen to the outer surface, such that the plane is tangential to both the circumference and the length of the inner surface; a plurality of protrusion members extending from the inner surface into the lumen for securely engaging a catheter; and a locking mechanism associated with the surfaces of the slit, wherein the device has a first open configuration and a second closed configuration such that the opposed surfaces are in contact with each other in the second closed configuration, and wherein the member comprises a hydrogel having a compliance matched to tissue to which the device is engaged, and an antimicrobial agent.

2. The device of claim 1, wherein the locking mechanism is selected from the group consisting of adhesives, straps, and protrusion hole couplings.

3. The device of claim 1, wherein the lumen has a diameter of between about 1 mm and about 10 mm.

4. The device of claim 1, wherein the hydrogel is comprised of a material selected from a group consisting of silicone, polyurethane, polycarbonate, polyvinyl alcohol, chitosan, chitin, collagen, gelatin, polyvinylpyrrolidone, and oxycellulose.

5. The device of claim 1, wherein the antimicrobial agent is selected from the group consisting of antibiotics, chlorhexidine gluconate, chlorhexidine acetate, chlorhexidine diacetate, iodine, peroxide, triclosan, benzalkonium chloride, octinidene, ethanol, silver halides, silver salts, and silver.

6. The device of claim 1, wherein the device further comprises a coating comprising an antimicrobial agent.

7. The device of claim 1, wherein the hydrogel is comprised of a material selected from a group consisting of silicone, polyurethane, polycarbonate, polyvinyl alcohol, chitosan, chitin, collagen, gelatin, polyvinylpyrrolidone, and oxycellulose.

8. A device for preventing catheter-related urinary tract infections, the device comprising:

a cylindrical member having first and second opposed ends, a lumen extending through the member, an inner surface about the lumen such that the lumen communicates with openings in the first and second ends, wherein the inner surface has a circumference and a length, and an outer surface, wherein the inner surface and the outer surface define a body wall, a slit defining a plane that extends out from the lumen to the outer surface through the body wall, such that the plane is tangential to both the circumference and the length of the inner surface, the slit having opposed faces that extend from the inner surface to the outer surface of the member for at least a portion of the length of the device, wherein the slit is self-locking such that the faces are in contact with each other, a plurality of protrusion members extending from the inner surface into the lumen for securely engaging a catheter, and wherein the member comprises a hydrogel having a compliance matched to tissue to which the device is engaged and an antimicrobial agent.

9. The device of claim 8, wherein the device has a first configuration and a second configuration.

10. The device of claim 9, wherein the first configuration is open and the second configuration is closed.

11. The device of claim 8, wherein the lumen has a diameter of between about 1 mm and about 10 mm.

12. The device of claim 8, wherein the first or second end of the device has a concave surface.

13. The device of claim 8, wherein the first or second end has a convex surface.

14. The device of claim 8 wherein the antimicrobial agent is selected from the group consisting of antibiotics, chlorhexidine gluconate, chlorhexidine acetate, chlorhexidine diacetate, iodine, peroxide, triclosan, benzalkonium chloride, octinidene, ethanol, silver halides, silver salts, and silver.

15. The device of claim 8 wherein the device further comprises a coating comprising an antimicrobial agent.

* * * * *